United States Patent [19]

Lanzilotta et al.

[11] 4,246,348
[45] Jan. 20, 1981

[54] MICROBIOLOGIC CONVERSION OF L-GALACTONATE INTO 2-KETO L-GALACTONATE

[75] Inventors: Raymond P. Lanzilotta, Danbury; Michael K. Weibel, West Redding, both of Conn.

[73] Assignee: Novo Laboratories, Inc., Wilton, Conn.

[21] Appl. No.: 953,793

[22] Filed: Oct. 23, 1978

[51] Int. Cl.³ ............................................... C12P 7/58
[52] U.S. Cl. ................................ 435/137; 435/847; 435/874; 435/876; 435/881; 435/822
[58] Field of Search ................... 195/30, 47; 435/137

[56] References Cited

U.S. PATENT DOCUMENTS

| | | | |
|---|---|---|---|
| 2,277,716 | 3/1942 | Lockwood et al. | 195/30 X |
| 2,338,534 | 1/1944 | Pasternack et al. | 195/30 X |
| 2,917,435 | 12/1959 | Perlman | 195/30 |

OTHER PUBLICATIONS

Laskin et al., Handbook of Microbiology, vol. III Microbial Products, 1973, CRC Press: Cleveland pp. 43, 44, 48–50.

Wallen et al., Type Reactions in Fermentation Chemistry, May 1959, ARS–71–13, Agri. Res. Service: USDA, pp. 31–41.

Braverman, Introduction to the Biochemistry of Foods, 1963, Elsevier Publ. Co.: New York, p. 210.

Primary Examiner—Joseph M. Golian
Attorney, Agent, or Firm—Fidelman, Wolffe & Waldron

[57] ABSTRACT

A metabolic conversion of L-galactonic acid into 2-Keto-L-galactonic acid by cultivating a microorganism in the presence of an L-galactonate. This reaction is an important step in synthesis of Vitamin C from substances that can be obtained from pectin.

6 Claims, No Drawings

MICROBIOLOGIC CONVERSION OF L-GALACTONATE INTO 2-KETO L-GALACTONATE

This invention relates to the synthesis of L-ascorbic acid (vitamin C) from pectins and, more particularly, to the conversion of L-galactonic acid, a material obtainable from pectin, into 2-keto-L-galactonic acid, a chemical precursor of L-ascorbic acid.

BACKGROUND OF THE INVENTION

The synthesis of vitamin C from pectin as the starting material involves a reaction sequence long known to the art, being for example described in Research Paper RP 1594 entitled "Synthesis of Vitamin C from Pectin Substances" by H. S. Isbell (Journal of Research of the National Bureau of Standards, Vol. 33, July, 1944, pp. 45–61). In theory, this conversion sequence offers the advantage of commencing with rather inexpensive widely available agriculture by-products (e.g. beet pulp or citrus pulp). In commercial practice, however, vitamin C is synthesized from glucose.

The inventors herein have reinvestigated the conversion of pectin substances into Vitamin C and have concluded that one major step of the sequence, namely, conversion of L-galactonic acid into 2-keto-L-galactonic acid is difficult to carry out with high yield by chemical procedures, but might be carried out microbiologically. The microbiologic reaction offers considerable promise for reducing conversion cost substantially.

RATIONALE OF THE INVENTION

The assumption underlying this invention is that metabolism of pectic substances by microorganisms could well proceed through previously unknown metabolic pathways involving the conversion of L-galactonic acid to 2-keto-galactonic acid. Although L-galactonic acid as such is not prevalent in nature, closely related biodegradable materials such as pectin are prevalent. Accordingly, it was believed reasonable to hope that the desired conversion of L-galactonic acid to 2-keto-L-galactonic acid might take place within microorganisms.

The scientific reality of the assumptions underlying this invention are susceptable to verification by screening microorganisms for growth on L-galactonic acid as the sole source of carbon for the microorganism. Those microorganisms surviving growth on an L-galactonic acid substrate, are tested thereafter for production of 2-keto-galactonic acid.

A limited screening program established that the metabolic pathway postulated herein does exist. Strains from several genera of microorganisms can metabolize L-galactonic acid via pathways involving 2-keto-L-galactonic acid. Measurable amounts of 2-keto-galactonic acid appeared in the nutrient medium and moreover with some microorganisms seemed to accummulate in the nutrient medium.

PRACTICE OF THE INVENTION

The process of this invention involves subjecting L-galactonic acid itself or an equivalent thereof such as L-galactono-1,4-lactone or non-toxic water soluble salts, notably sodium L-galactonate, all being hereinafter referred to as L-galactonate, to microbiological oxidation by cultivating a microorganism that metabolically converts L-galactonate into 2-keto-L-galactonate in an L-galactonate containing medium, then after the 2-keto-L-galactonate has been elaborated in the medium, separating the medium from the microorganism. The metabolic product may be 2-keto-L-galactonic acid, or a salt thereof, all of which are herein referred to as 2-keto-L-galactonate. The 2-keto-L-galactonate is then recovered from the separated medium. The product 2-keto-L-galactonic acid may be recovered from cell free (filtered) broth by standard procedures including solvent precipitation (e.g. with methanol), insoluble salt precipitation (e.g. as calcium salt) or adsorption (e.g. on an anion exchange resin).

DETAILED DISCUSSION OF THE INVENTION

The screening program employed to establish that the L-galactonate may be metabolically converted into 2-keto-L-galactonate involved efforts to isolate candidate microorganisms from garden soil samples and from decaying wood. In addition, tests were carried out on microorganism samples from culture collections.

The initial test procedure involved adding a soil sample, or a sample of decaying vegetable matter to a growth medium containing the L-galactonate as the only carbon source for the microogranism, then incubating the mixture. Under these test conditions microorganisms capable of utilizing the L-galactonate should become predominant in the culture broth. The details of such a screening program are set out hereafter as Examples A and B.

A suitable mineral salt solution (MSS) formulation for the screening program is:

| | |
|---|---|
| $NaH_2PO_4 \cdot H_2O$ | 1.2 g |
| $CaCl_2$(anhydrous) | 0.01 g |
| $Fe(NH_4)_2(SO_4)_2 \cdot 6H_2O$ | 0.0005 g |
| $NH_4NO_3$ | 0.2 g |
| $MgSO_4$ (anhydrous) | 0.05 g |
| $K_2HPO_4 \cdot 3H_2O$ | 0.25 g |
| trace element solution | 1 ml |
| carbon source solution | 100 ml |
| deionized $H_2O$ | 900 ml |
| Trace Element Solution Composition | |
| $H_3BO_3$ | 2.86 g |
| $MnCl_3 \cdot 4H_2O$ | 1.18 g |
| $ZnSO_4 \cdot 7H_2O$ | 0.22 g |
| $CuSO_4 \cdot 5H_2O$ | 0.08 g |
| $(NH_4)_2M_0O_4 \cdot H_2O$ | 0.02 g |
| deionized $H_2O$ | 100 ml |

EXAMPLE A

The MSS nutrient minus the carbon source solution was sterilized by autoclaving at 121° C. for 20 minutes.

The carbon source solution was prepared by dissolving 20 grams of crystalline L-galactono-1, 4-lactone in approximately 80 ml of deionized water. This solution was adjusted to pH 6.5 by gradual addition of concentrated NaOH, an expedient necessary to neutralize the acid that results from a gradual room temperature opening of the lactone ring to form the corresponding 4-hydroxy-1-carboxylic acid (i.e. L-galactonic acid) in aqueous solution. This solution of sodium-L-galactonate was brought to final volume of 100 ml and then filter sterilized. The now sterile carbon source solution was added to the mineral salt solution (MSS) to give finally a nutrient medium containing about 2% w/v of the hydrolyzed lactone.

Two Erlenmeyer flasks (250 ml) were prepared, each containing 50 ml. of the culture medium described above. One of the two flasks received additionally 5 mg of the antifungal antibiotic cyclohexamide prepared as a concentrated, filter sterilized, aqueous solution (5 mg per ml). Two similar flasks were also prepared except they were formulated without a carbon source; they served as controls. All four flasks were then incubated with 1 gm each of the same microorganism source material, which variously included garden soil samples, and decaying hickory wood samples. The flasks were then incubated at 28° C. on a rotary shaker (2.5 cm excursion) at 250 rpm. After 24 hours, 1 ml of culture broth from each flask was transferred to fresh culture medium of identical composition and incubated as before. After 24 hours, a second transfer was made, then incubated as before, and so on up, to four transfers. The following observations can be made after the fourth transfer in a great many instances:

1. The flasks which contained only mineral salts and no carbon source were essentially clear, with no signs of microbial growth (turbidity).
2. The flasks which contained only mineral salts plus antibiotic but no other carbon source were slightly turbid; (apparently microorganisms were using the cyclohexamide as substrate).
3. The flasks containing L-galactonic acid both with and without antibiotic were quite turbid, indicating the presence of one or more microorganisms able to grow on the L-galactonic acid substrate.
4. There was no readily apparent difference between the flask containing L-galactonate together with the anti-fungal antibiotic and the flask containing no antibiotic.

EXAMPLE B

Isolation of L-galactonic Acid Utilizing Microorganisms

Petri plates containing neutralized L-galactonic acid-MSS agar were prepared. Streak plates were made from enrichment cultures obtained as described in Example A. Subplating was conducted to obtain pure microorganism cultures from the different morphologically distinguishable colony types on the streak plates. Incubations were at 28° C., except where a slow rate of development was desirable, in which instance the Petri plates were kept at room temperature. This procedure yielded several diverse isolates from the soil samples, including an Erwinia species never previously described and several strains of *Erwinia herbicola*. A decaying hickory wood sample yielded an isolate (HT-1) later identified as *Pseudomonas fluorescens*.

In addition, following the enrichment procedure described above except that transfers were made every 48 hours rather than every 24 hours, other bacterial isolates were recovered from streak plates, including a strain of *Pseudomonas cepacia* and a strain of *Citrobacter amalonaticus*. Also, recovered was a strain of a microorganism identifiable as CDC biotype VE-2 belonging to a group resembling *Chromobacterium typhiflavum*.

In all instances the ability of the enrichment culture isolates to grow on L-galactonate as the sole source of carbon and energy was confirmed by making back transfers to Erlenmeyer flasks containing mineral salt solution (MSS) with L-galactonate as the only carbon source for the microorganism and later an observation of microorganism growth after incubation on rotary shakers (28° C. at 200 rpm).

EXAMPLE C

Survey of Known Microorganisms from Culture Collections for Ability to Utilize L-galactonic Acid as a Sole Source of Carbon The search to find L-galactonate utilizers was expanded to include strains of selected taxonomically defined bacteria obtained from culture collections (including ATCC, NRRL, QM). The supposition was that any L-galactonate utilizers are at least potential producers of 2-keto-L-galactonate, the desired product. The overall experimental approach was essentially the same as described above for confirmation of L-galactonate utilization by purified enrichment isolates.

Specifically, agar slants of each test culture were prepared using the same medium as used for stock culture maintenance. Surface growth was harvested after incubation at 28° C. for 24 to 48 hours, the exact period depending on microbial growth rate. The harvested material was used to inoculate Erlenmeyer shake-flasks containing mineral salt solution (MSS) with sodium-L-galactonate (L-galactano-1, 4-lactone neutralized with sodium hydroxide) at 2% w/v as the sole carbon source therein. Appropriate control flasks were also inoculated.

Some 30 species of microorganism were tested by the above described procedure without success, including a Bacillus, a Xanthomonas, a Micrococcus, five species of Acetobacter and about 15 species of Pseudomonas. It was found, however, that with one strain of *Serratia marcescens* received from a culture collection a significant increase in turbidity occurred during the 120 hour incubation period evidencing thereby growth.

The ability to metabolize L-galactonate may be a strain specific property in microorganisms. Of the two strains of *S. marcescens* received from culture collections and tested, only one caused the turbidity increase. In addition, one strain of *Ps. fluorescens* obtained from a culture collection did not metabolize the L-galactonate whereas the hickory wood derived strain (HT-1) of this species did metabolize L-galactonate.

Since the ability of several diverse microorganism species to metabolize the L-galactonate was believed to be established by the screening procedure described above and numerous strains of suitable microorganisms were made available by the screening program, it then became possible to ascertain whether 2-keto-L-galactonate is an intermediate in the metabolism of L-galactonate. The test procedure involved suspending the cells in aqueous L-galactonate, (i.e. free of added nitrogen nutrient). In such an environment the microorganism may carry out some enzymatic transformation, but not all of the metabolism associated with growth. During cultivation of the microorganism under such test circumstances, an accumulation in solution in the culture medium of early intermediates from the catabolism of L-galactonate is probable. Evidence of accumulation of 2-keto-galactonate was observed for most of the enrichment culture isolates.

The methodology is exemplified below:

EXAMPLE D

Evidence Indicating 2-keto-L-galactonic Acid is an Intermediate in the Metabolism of L-galactonic Acid
L-galactonate-MSS agar slants of the test cultures were prepared. After 72 hours of incubations, surface growth from each slant was harvested and used to inoculate 40 ml of Supplemented Nutrient Broth (SNB) contained in 250 ml Erlenmeyer flasks. The composition of SNB is as follows:

| | |
|---|---|
| glucose | 10g |
| yeast extract (Difco) | 10g |
| nutrient broth, dehydrated (Difco) | 8g |
| Deionized water | 1000 ml |

After 48 hours of incubation (28° C.) on a rotary shaker (250 rpm) cells were harvested by centrifugation in sterile plastic centrifuge tubes. The supernatant fluid from each culture was decanted and the cells were aseptically resuspended in 20 ml of sterile aqueous sodium-L-galactonate (2% galactono-1, 4-lactone adjusted to pH 6.5 with concentrated sodium hydroxide and sterilized by autoclaving) contained in a 125 ml Erlenmeyer flask. All flasks were incubated as before (250 rpm; 28° C.) and 2 ml samples were periodically withdrawn and freed of cells by centrifugation. Aliquots 20 µl) of the cellfree broths were then analyzed by thin-layer electrophoresis (0.1 M phosphate buffer; pH 2.5; 600 volts; silica gel-GF plates). In all cases, authentic, synthetic 2-keto-L-galactonic acid was spotted on the plates with the experimental samples. Spots were visualized under short wave UV light, after spraying with 1% semicarbazide in 80% aqueous ethanol followed by heating.

In addition, the samples taken from each culture after 24 and 48 hours of incubation were combined, lyophilized and then derivatized (silyl ethers) and thereafter analyzed by quantitative gas chromatography against derivatized authentic 2-keto L-galactonic acid.

The thin-layer electrophoresis results indicated for numerous test cultures, an accumulation of a ketone having the same $R_f$ value as the authentic 2-keto-L-galactonic acid. Moreover, supporting evidence of 2-keto-L-galactonate accumulation was obtained by gas chromatographic analyses. Thus a compound having the same retention time as the silylation derivative of authentic 2-keto-L-galactonic acid was found in the culture broth from: P. cepacia (SL-1), E. herbicola (SL-3), CDC Biotype VE-2 (SL-4), and the Erwinia species (SL-6). Reduction of the gas chromatographic data to concentration indicated the following accumulations of a 2-keto-L-galactonate:

| | µg/ml |
|---|---|
| SL-1 | 17.7 |
| SL-3 | 113 |
| SL-4 | 19.9 |
| SL-6 | 90.8 |

Practice of this invention takes advantage of the accumulation of 2-keto-L-galactonate in the culture medium in growing cultures, as well as in resting cell (replacement cultures).

Subcultures of the various microorganism strains herein described as suitable for practice of this invention are on deposit in the U.S.D.A. Agricultural Research Service culture collection with the following NRRL accession numbers.

| Name | Strain Designation | NRRL Number |
|---|---|---|
| CDC- Biotype VE-11 | SL-4 | B-11364 |
| Citrobacter amalonaticus | SL-2 | B-11365 |
| Erwinia herbicoia | SL-3 | B-11366 |
| Erwinia herbicola | SL-7 | B-11367 |
| Erwinia sp. nov. | SL-6 | B-11368 |
| Pseudomonas cepacia | SL-1 | B-11369 |
| Pseudomona fluorescens | HT-1 | B-11370 |

For further understanding of this invention the following examples are provided describing the metabolic production of 2-keto-L-galactonate from L-galactonate.

EXAMPLE 1—ERWINIA HERBICOLA STRAIN SL-3.

The SL-3 culture was prepared as a sodium-L-galactonate-MSS agar slant. After 24 hours of incubation at 28° C. surface growth was harvested into 5 ml of sterile water, one ml of which was used to inoculate a 250 ml Erlenmeyer flask containing 50 ml of 0.5% (w/v) sterile sodium-L-galactonate-MSS broth. The flask was then incubated (28° C.) on a rotary shaker (200 rpm). Two milliliter samples were withdrawn after 0, 6, 24, 126, 150, 174 and 222 hours of incubation. The samples were freed of cells by centrifugation (3000 rpm) for 20 minutes. A portion (20 µl) of each sample was analyzed by thin-layer electrophoresis for accumulation of 2-keto-L-galactonate. In addition, the 150, 174 and 222 hour samples (6 ml in all) were combined, lyophilized and derivatized (silation) for analysis by gas-chromatography.

The thin-layer electrophoresis analysis qualitatively indicated that 2-keto-L-galactonate accumulation increased with time of incubation, reaching a maximum between 150 and 175 hours. The quantitative gas-chromatographic analysis showed the lyophilized sample contained 32 µg/ml of 2-keto-L-galactonic acid.

EXAMPLE 2 SERRATIA MARCESCENS STRAIN 398 RPL

The overall procedure was essentially the same as described above for Erwinia herbicola, SL-3 except that the agar slant was incubated for four days at 28° C. instead of 24 hours. Also, 1 ml samples were taken at 96, 120, 144 and 260 hours. As before, the samples were freed of cells by centrifugation. Aliquots (20 µl) of the cell-free broth were spotted for thin-layer electrophoretic analysis. In addition, the 96, 120 and 196 hour samples (3 ml) were combined, lyophilized and derivatized for analysis by gas chromatography.

The thin-layer electrophoresis analysis indicated increasing accumulations of 2-keto-L-galactonate throughout the incubation period of 260 hours. The quantitative gas-chromatographic analysis showed that the lyophilized sample contained 9.2 µg/ml. of the 2-keto-L-galactonate.

Although yields described in the foregoing examples represented just under 1% and the foregoing examples nevertheless represent the best mode of this invention presently known, skilled workers in the art will not confuse such yields with future realities. The yields achieved herein from wild and depository microorganism strains are believed to be significant, even exciting, and in fact are not believed to differ materially from the test result yields initially obtained for what since have become large volume microbiologically products. Optimization of culture conditions and use of known to the art mutation and strain selection techniques can be expected to increase yields dramatically. (See for example Thoma, "Use of Mutagens in the Improvement of Production Strains of Microorganisms" in Folio Microbiologica, Vol. 16, 197–204, 1977).

Allusion has been made above that the enzyme or enzyme system that converts L-galactonate to 2-keto L-galactonate is believed to be induced, while an enzyme system or systems involved in subsequent metabolism of 2-keto-L-galactonate is believed to be constitutive. Such belief is substantiated by comparative results of oxygen uptake studies for the same culture under two different conditions.

The same microorganism was cultured either in the presence of L-galactonate or an alternative carbon source, e.g. glucose. After harvesting, washing and resuspension both cultures evidenced an immediate significant oxygen uptake when 2-keto-galactonate was added to the suspension media. The increase in oxygen uptake indicated that constitutively the microorganism strain is capable of aerobic metabolism the 2-keto-L-galactonate. On the other hand a like set of experiments where L-galactonate was incorporated into the suspension media exhibited significant differences in the patterns of oxygen uptake. The microorganism specimen that previously had been grown on L-galactonate exhibited a prompt and significant oxygen uptake, while the microorganism specimen that had been grown on a dissimilar carbon source e.g. glycerol, exhibited a delayed oxygen uptake response. This difference in oxygen uptake response indicates that at least one enzyme system involved in the metabolism of L-galactonate is induced, and also that 2-keto-L-galactonate may well be an intermediate in the metabolism sequence.

It is noted that the oxygen uptake studies evidenced a far greater conversion of L-galactonate than is indicated by the yield of 2-keto-L-galactonate in the culture medium. It is believed that the 2-keto-L-galactonate constitutes an early and critical intermediate in the metabolic process utilizing the L-galactonate (as the sole carbon source). In fact, the presence of what currently are structurally unknown metabolites accumulating in the culture medium (in addition to the 2-keto-L-galactonic acid) was indicated by the analytical test results.

What is claimed is:

1. A metabolic method for converting L-galactonic acid to 2-keto-L-galactonic acid which comprises cultivating a microorganism strain which converts L-galactonate into 2-keto-L-galactonate in the presence of L-galactonate until 2-keto-L-galactonate is elaborated in the culture medium then separating the 2-keto-L-galactonate containing medium from the microorganism.

2. The process of claim 1 wherein the microorganism strain is from the species *Erwinia herbicola*.

3. The process of claim 1 wherein the microorganism strain is from the species *Pseudomonas cepacia*.

4. The process of claim 1 wherein the microorganism strain is from the species *Pseudomonas fluorescens*.

5. The process of claim 1 wherein the microorganism strain is from the species *Serratia marcescens*.

6. The process of claim 1 wherein the microorganism strain is from the species *Citrobacter amalonaticus*.

* * * * *